United States Patent
Choi

(10) Patent No.: US 10,168,891 B2
(45) Date of Patent: Jan. 1, 2019

(54) DISPLAY DEVICE AND CONTROLLING METHOD THEREOF

(71) Applicant: LG ELECTRONICS INC., Seoul (KR)

(72) Inventor: Kyungdong Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 105 days.

(21) Appl. No.: 14/858,805

(22) Filed: Sep. 18, 2015

(65) Prior Publication Data

US 2016/0357386 A1    Dec. 8, 2016

(30) Foreign Application Priority Data

Jun. 3, 2015   (KR) .................. 10-2015-0078378

(51) Int. Cl.
*G06F 3/0488* (2013.01)
*G04G 9/00* (2006.01)
(Continued)

(52) U.S. Cl.
CPC ........ *G06F 3/0488* (2013.01); *A61B 5/02438* (2013.01); *A61B 5/4806* (2013.01);
(Continued)

(58) Field of Classification Search
CPC ........ G06F 1/3265; G06F 1/3206; G06F 3/01; G06F 3/04847; G06F 3/048;
(Continued)

(56) References Cited

U.S. PATENT DOCUMENTS 5,444,671 A * 8/1995 Tschannen ............ G04G 21/04
   340/7.21
6,477,117 B1 * 11/2002 Narayanaswami .. G04G 13/026
   368/224
(Continued)

FOREIGN PATENT DOCUMENTS

CN   1267990 A   9/2000
CN   1929664 A   3/2007
(Continued)

OTHER PUBLICATIONS

"Analog Clock-7," Download.com, XP055311815, http://download.cnet.com/Analog-Clock-7/3000-2257_4-10915266.html, Oct. 30, 2010 (retrieved from the Internet on Oct. 18, 2016), p. 1-3.

*Primary Examiner* — Lun-Yi Lao
*Assistant Examiner* — Johny Lau
(74) *Attorney, Agent, or Firm* — Birch, Stewart, Kolasch & Birch, LLP

(57) ABSTRACT

A display device including a touch screen configured to display an analog watch screen; a wireless communication unit configured to receive data from an external device; a sensing unit configured to sense at least one of a motion of the display device and biometric state information of a user; and a controller configured to switch the analog watch screen to a digital watch screen in response to at least one of a predetermined touch input on the touch screen, an amount of data received from the external device, a specific motion of the display device sensed by the sensing unit, and specific biometric state information of the user sensed by the sensing unit.

16 Claims, 16 Drawing Sheets

(51) Int. Cl.

| | | |
|---|---|---|
| *H04M 1/725* | (2006.01) | |
| *G06F 3/0481* | (2013.01) | |
| *G06F 3/01* | (2006.01) | |
| *G06F 3/041* | (2006.01) | |
| *G06F 3/042* | (2006.01) | |
| *G06K 9/00* | (2006.01) | |
| *G04G 21/08* | (2010.01) | |
| *A61B 5/00* | (2006.01) | |
| *A61B 5/024* | (2006.01) | |
| *G06F 1/16* | (2006.01) | |
| *H04B 1/3827* | (2015.01) | |

(52) U.S. Cl.
CPC .............. *A61B 5/681* (2013.01); *A61B 5/742* (2013.01); *G04G 9/0064* (2013.01); *G04G 21/08* (2013.01); *G06F 3/016* (2013.01); *G06F 3/0412* (2013.01); *G06F 3/0416* (2013.01); *G06F 3/0421* (2013.01); *G06F 3/04817* (2013.01); *G06K 9/00013* (2013.01); *G06K 9/00885* (2013.01); *H04M 1/72519* (2013.01); *G06F 1/163* (2013.01); *H04B 2001/3861* (2013.01); *H04M 1/7253* (2013.01); *H04M 1/72547* (2013.01); *H04M 1/72597* (2013.01); *H04M 2250/12* (2013.01); *H04M 2250/60* (2013.01)

(58) Field of Classification Search
CPC .... G06F 3/0488; G06F 3/04817; G06F 3/016; G06F 3/0412; G06F 3/0416; G06F 3/0421; G06F 1/163; G04G 13/026; G04G 21/04; G04G 9/0064; G04G 21/08; A61B 5/0015; A61B 5/4806; A61B 5/742; A61B 5/02438; A61B 5/681; H04M 1/72519; H04M 1/7253; H04M 1/72547; H04M 1/72597; H04M 2250/12; H04M 2250/60; H04B 2001/3861; G06K 9/00013; G06K 9/00885
See application file for complete search history.

(56) References Cited

U.S. PATENT DOCUMENTS

| | | | |
|---|---|---|---|
| 9,009,516 B1 * | 4/2015 | Gabayan | ............... G06F 1/3206 |
| | | | 702/141 |
| 2009/0186659 A1 | 7/2009 | Platzer | |
| 2009/0249247 A1 * | 10/2009 | Tseng | ............... H04M 1/72552 |
| | | | 715/808 |
| 2014/0101472 A1 * | 4/2014 | Rohrweck | ............. G06F 1/3265 |
| | | | 713/323 |
| 2014/0139422 A1 * | 5/2014 | Mistry | .................... G06F 3/014 |
| | | | 345/156 |
| 2014/0180595 A1 * | 6/2014 | Brumback | ........... A61B 5/0015 |
| | | | 702/19 |
| 2014/0215246 A1 | 7/2014 | Lee et al. | |
| 2014/0240122 A1 | 8/2014 | Roberts et al. | |
| 2015/0049033 A1 | 2/2015 | Kim et al. | |
| 2016/0179353 A1 * | 6/2016 | Iskander | ............. G06F 3/04847 |
| | | | 715/765 |

FOREIGN PATENT DOCUMENTS

| | | |
|---|---|---|
| CN | 101911176 A | 12/2010 |
| CN | 104375774 A | 2/2015 |
| EP | 1 035 710 A1 | 9/2000 |
| EP | 1 762 968 A1 | 3/2007 |

* cited by examiner

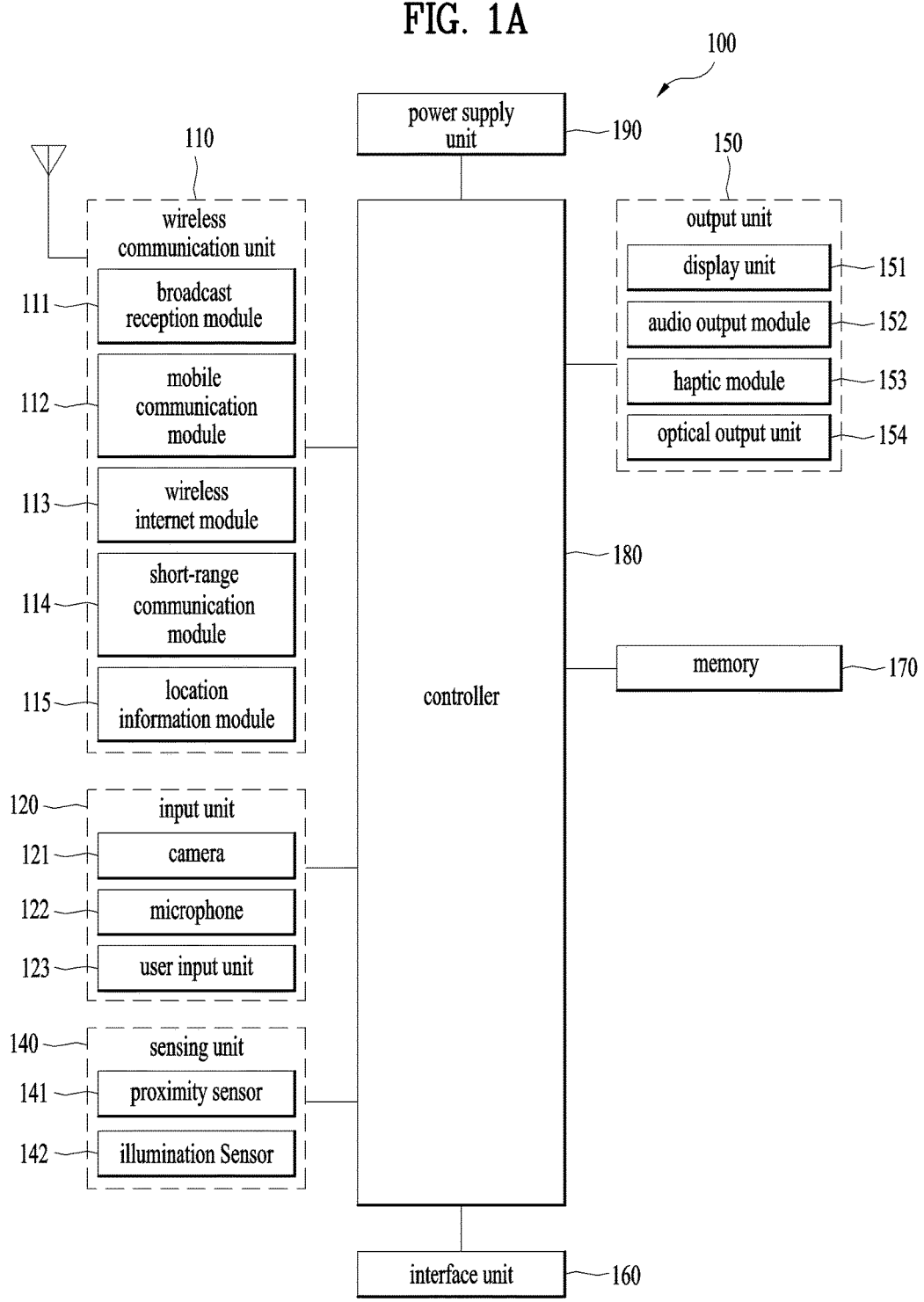

(a)  (b)

US 10,168,891 B2

DISPLAY DEVICE AND CONTROLLING METHOD THEREOF

Pursuant to 35 U.S.C. § 119(a), this application claims the benefit of earlier filing date and right of priority to Korean Application No. 10-2015-0078378, filed on Jun. 3, 2015, the contents of which are hereby incorporated by reference herein in their entirety.

BACKGROUND OF THE INVENTION

Field of the Invention

The present invention relates to a display device, and more particularly, to a display device and controlling method thereof.

Discussion of the Related Art

Generally, terminals can be classified into mobile/portable terminals and stationary terminals. In particular, the mobile terminals can be further classified into handheld terminals and vehicle mounted terminals. Recently, functions of a mobile terminal tend to be diversified. For instance, the diversified functions include a function of data and audio communication, a function of photographing and recording a video through a camera, a function of audio recording, a function of music file play through a speaker system, a function of outputting image or video through a display unit, and the like. A prescribed terminal is further equipped with an electronic game play function or performs a multimedia player function. Particularly, a recent mobile terminal can receive multicast signals for providing visual contents such as a broadcast, a video, a television program and the like.

As functions of the terminal are becoming diversified, the terminal tends to be implemented as a multimedia player provided with complex functions such as photographing of photos or videos, playback of music or video files, game play, broadcast reception and the like for example.

Meanwhile, a terminal can display an analog watch screen or a digital watch screen. A user may prefer the analog watch screen in aspect of design of terminal UI. However, in order to check necessary information, the digital watch screen may be more convenient than the analog watch screen. Thus, the demand for a technology of switching the analog watch screen and the digital watch screen to each other quickly and conveniently is increasingly rising.

SUMMARY OF THE INVENTION

Accordingly, embodiments of the present invention are directed to a display device and controlling method thereof that substantially obviate one or more problems due to limitations and disadvantages of the related art.

An object of the present invention is to provide a display device and controlling method thereof, by which necessary data can be displayed by switching a displayed analog watch screen to a digital watch screen in case of occurrence of a preset event.

Additional advantages, objects, and features of the invention will be set forth in the disclosure herein as well as the accompanying drawings. Such aspects may also be appreciated by those skilled in the art based on the disclosure herein.

To achieve these objects and other advantages and in accordance with the purpose of the invention, as embodied and broadly described herein, a display device according to an embodiment of the present invention may include a display unit configured to display an analog watch screen, an input unit configured to receive an input of a user's command, a communication unit configured to receive data from an external device, a sensing unit configured to detect at least one of a motion information of the display device and a state information of a user, and a controller determining whether a preset condition is met based on at least one selected from the group consisting of the input user's command, the received data, the detected motion information of the display device and the detected state information of the user, the controller, if the preset condition is met, switching the analog watch screen to a digital watch screen.

In another aspect of the present invention, a method of controlling a display device according to an embodiment of the present invention may include the steps of displaying an analog watch screen, receiving at least one information selected from the group consisting of a user's command, data of an external device, a motion information of the display device and a state information of a user, determining whether a preset condition is met based on at least one selected from the group consisting of the user's command, the data of the external device, the motion information of the display device and the state information of the user, and if the preset condition is met, switching the analog watch screen to a digital watch screen.

Effects obtainable from the present invention may be non-limited by the above mentioned effect. And, other unmentioned effects can be clearly understood from the following description by those having ordinary skill in the technical field to which the present invention pertains. Both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. The above and other aspects, features, and advantages of the present invention will become more apparent upon consideration of the following description of preferred embodiments, taken in conjunction with the accompanying drawing figures. In the drawings:

FIG. 1A is a block diagram illustrating a mobile terminal related to the present invention;

DETAILED DESCRIPTION OF THE INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Although the terms first, second, etc. may be used herein illustrating various elements, these elements should not be limited by these terms. These terms are generally only used to distinguish one element from another. When an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like. By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1B:
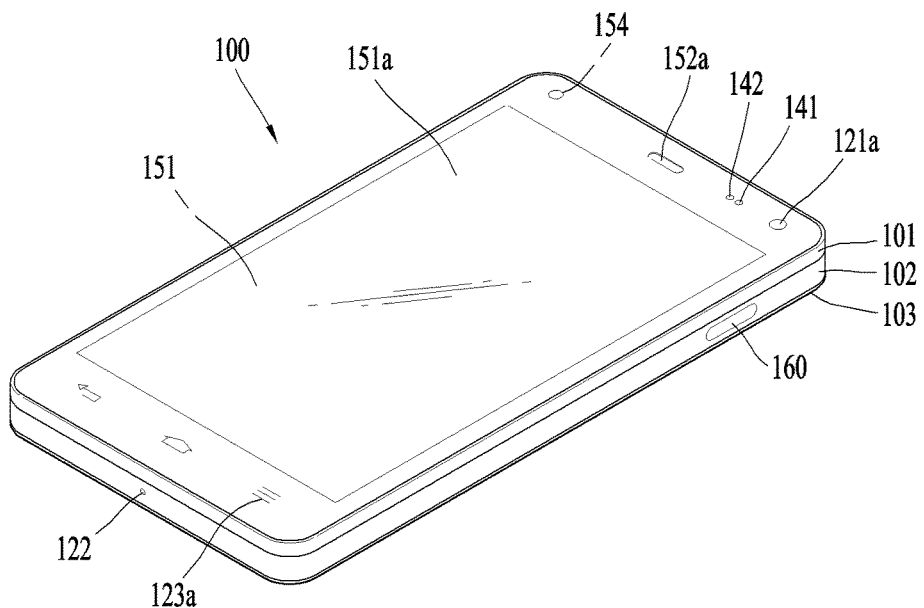
FIG. 1B and FIG. 1C are conceptional diagrams illustrating one example of a mobile terminal related to the present invention viewed in different directions, respectively.
Figure 1C:
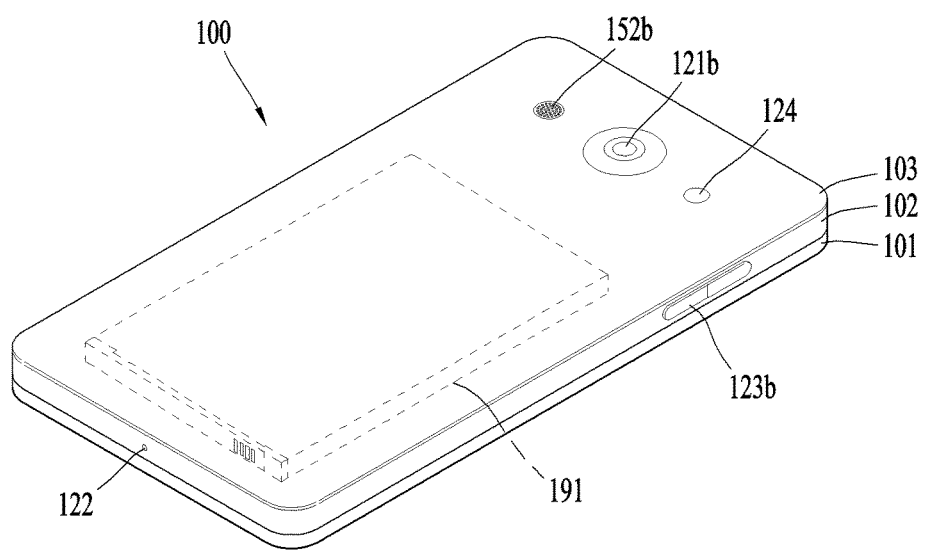

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. Implementing all of the illustrated components is not a requirement, and that greater or fewer components may alternatively be implemented. Referring now to FIG. 1A, the mobile terminal 100 is shown having wireless communication unit 110 configured with several commonly implemented components.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 can process or provide appropriate information or function to a user by processing signals, data, information and the like input or output through the above-mentioned components or running application programs saved in the memory 170.

The controller 180 can provide or process information or functions appropriate for a user by processing signals, data, information and the like, which are input or output by the various components depicted in FIG. 1A, or activating application programs stored in the memory 170. As one example, the controller 180 controls some or all of the components illustrated in FIG. 1A according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body. At least one portion of the above-mentioned components can cooperatively operate to embody operations, controls or controlling methods of the mobile terminal according to various embodiments mentioned in the following description. And, the operations, controls or controlling methods of the mobile terminal can be embodied on the mobile terminal by running at least one or more application programs saved in the memory 170.

Referring still to FIG. 1A, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies. Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which can exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal. As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. Further, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this instance, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others. As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 can sense which region of the display unit 151 has been touched. Here, the touch controller may be a component separate from the controller 180, the controller 180, and combinations thereof.

In some embodiments, the controller 180 can execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like. If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor. Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like. A signal output by the optical output module 154 may be implemented so the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 can typically control the general operations of the mobile terminal 100. For example, the controller 180 can set or release a lock state for restricting a user from inputting a control command with respect to applications when a status of the mobile terminal meets a preset condition. The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provides internal power and supply the appropriate power required for operating respective elements and components included in the mobile terminal 100. The power supply unit 190 may include a battery, which is typically rechargeable or be detachably coupled to the terminal body for charging. The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance. Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101. In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like. As an alternative to the example in which the plurality of cases form an inner space for accommodating components, the mobile terminal 100 may be configured such that one case forms the inner space. In this example, a mobile terminal 100 having a uni-body is formed so synthetic resin or metal extends from a side surface to a rear surface.

If desired, the mobile terminal 100 may include a waterproofing unit for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal 100 may be provided with the display unit 151, the first audio output unit 152a, the second audio output unit 152b, the proximity sensor 141, the illumination sensor 142, the light output unit 154, the first camera 121a, the second camera 121b, the first manipulating unit 123a, the second manipulating unit 123b, the microphone 122, the interface unit 160, and the like.

FIGS. 1B and 1C depict certain components as arranged on the mobile terminal. However, alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces. The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a. The first audio output module 152a may be implemented in the form of a speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this instance, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170. The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof. Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen. As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds. The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown. The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject. As shown in FIG. 1C, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like.

A typical wearable device can exchange data with (or cooperate with) another mobile terminal 100. In such a device, the wearable device generally has functionality that is less than the cooperating mobile terminal. For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 can transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Figure 2:
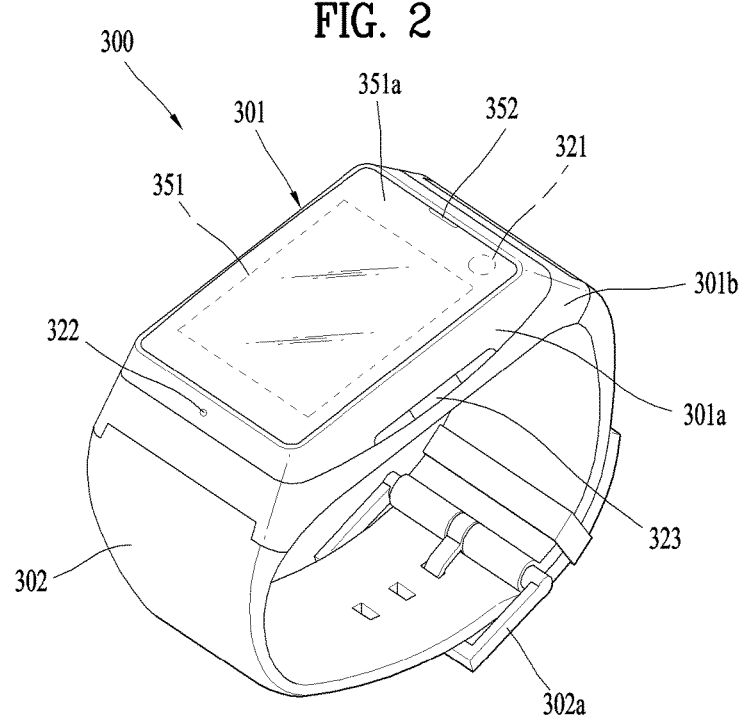
FIG. 2 is a perspective diagram illustrating one example of a mobile terminal of a watch type related to another embodiment of the present invention.

FIG. 2 is a perspective view illustrating one example of a watch-type mobile terminal 300 in accordance with another exemplary embodiment. As illustrated in FIG. 2, the watch-type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIGS. 1A-1C.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first case 301a to form a front surface of the terminal body together with the first case 301a.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion electrically connected to the antenna to extend a ground area. The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

Further preferred embodiments will be described in more detail with reference to additional drawing figures. It is understood by those skilled in the art that the present features can be embodied in several forms without departing from the characteristics thereof.

Figure 3:
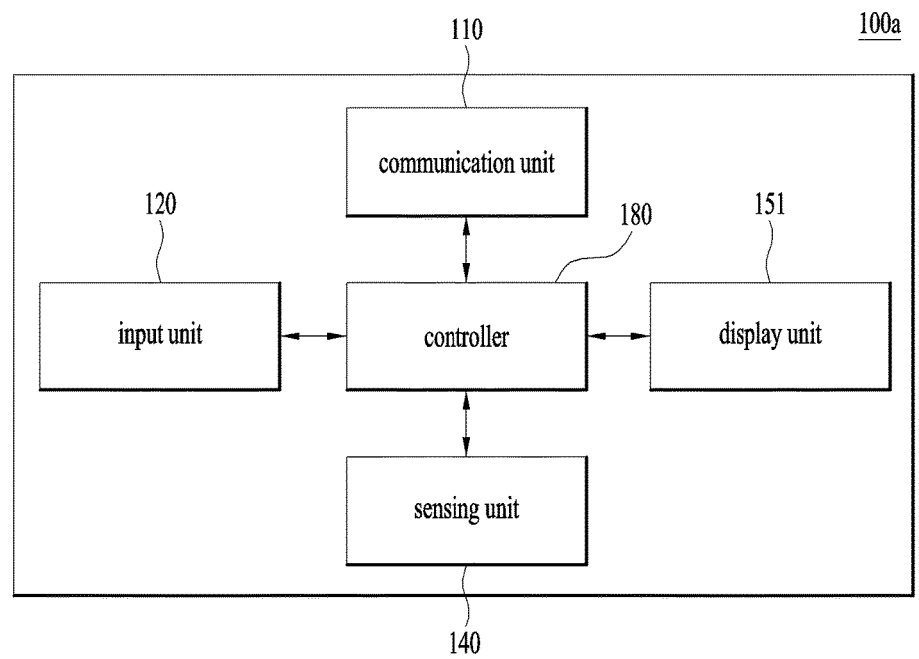
FIG. 3 is a block diagram of a display device according to one embodiment of the present invention.

FIG. 3 is a block diagram of a display device according to one embodiment of the present invention. Referring to FIG. 3, a display device 100a may include a communication unit 110, an input unit 120, a sensing unit 140, a display unit 151 and a controller 180.

The display unit 151 can display an analog watch screen. The display unit 151 can display a digital watch screen as well. The analog watch screen means a screen for displaying a time with an hour hand a minute hand. The analog watch screen may include a second hand as well. The analog watch screen may further include numerals indicating hours. Yet, the analog watch screen may include scales only without the numerals. In some cases, the display device 100a may include a physical hour hand and a physical minute hand.

In particular, the display device 100a includes the physical hour hand and the physical minute hand and may display the analog watch screen by displaying the numerals and scales to indicate a time on the display unit 151. The analog watch screen may further include additional data as well as time information. Further, the digital watch screen means a screen for displaying a time with numerals. The digital watch screen can further include additional information as well as the time. For instance, the display device 100a may include one of a smartphone, a wearable watch, and the like. If the display device 100a includes the wearable watch, the analog watch screen may be displayed as a full screen.

If the display device 100a includes the smartphone, the analog watch screen may be displayed as a full screen or a partial screen. If the display device 100a is the smartphone, the display device 100a may be enclosed with a case having a window. In particular, if the display device 100a is enclosed with the case, a partial region of the display unit 100a may be externally seen through the window. If the display device 100a is enclosed with the case, the analog watch screen may be displayed to correspond to a window region.

The input unit 120 receives a user's command. The input unit 120 may be embodied with a separate means provided to an outside of the display unit 151. For instance, the input unit 120 may include at least one of a microphone configured to receive an input of audio and a camera configured to receive an input of user's eyes, an input of a motion gesture and the like. Alternatively, the input unit 120 may be embodies with a touch sensor and can be disposed together with the display unit 151. In particular, the input unit 120 may be embodies with a touchscreen. If the input unit 120 receives a user's command, the controller 180 can perform an operation corresponding to the input command. For instance, when the display device 100a displays the analog watch screen, the display device 100a can set a touch input to a rotation center region, which becomes the center of rotations of the hour and minute hands, as a command for switching the analog watch screen to the digital watch screen. If the display device 100a receives an input of a touch gesture applied to the rotation center region of the hour and minute hands, the display device 100a can switch the displayed analog watch screen to the digital watch screen.

The communication unit 110 can receive data from an external device. For instance, the communication unit 110 can receive an incoming call from a counterpart or a text sent by a counterpart. Based on the data reception of the communication unit 110, the controller 180 can switch the analog watch screen to the digital watch screen.

The sensing unit 140 detects a surrounding environment of the display device 100a using at least one sensor loaded on the display device 100a and can then deliver the detected surrounding environment to the controller 180. The sensing unit 140 detects a user input and can then deliver the detected user input to the controller 180. Further, the sensing unit 140 may include at least one sensing means. For instance, the sensing means may include various sensing means such as a gravity sensor, a geomagnetic sensor, a motion sensor, a gyroscopic sensor, an acceleration sensor, an infrared sensor, an inclination sensor, an altitude sensor, an olfactory sensor, a temperature sensor, a depth sensor, an pressure sensor, a bending sensor, an audio sensor, a video sensor, a GPS (global positioning system) sensor, a touch sensor, a fingerprint sensor and the like as well as the proximity sensor 141 and the illumination sensor 142 shown in FIG. 1A. The above-listed various sensing means are commonly called the sensing unit 140. In particular, the sensing unit 140 senses various inputs and environment of a user and can then deliver the sensing results to enable the controller 180 to perform operations accordingly. The above-mentioned sensing means may be included as a separate element in the display device 100a or can be integrated into at least one or more elements to be included in the display device 100a.

The sensing unit 140 can detect a motion information of the display device, a state information of a user and the like. The sensing unit 140 can send the detected motion information of the display unit to the controller 180. Based on the information detected from the sensing unit 140, the controller 180 can determine whether a preset event occurrence reference is met. If the motion information of the display unit meets the preset event occurrence reference, the controller 180 triggers a corresponding event. According to one embodiment, if a motion of the display device 100a swaying over 5 seconds is detected, the display device 100a can be set to switch the analog watch screen to the digital watch screen.

If the display device 100a sways, the sensing unit 140 detects a motion of the display device 100a and can then deliver the detected motion to the controller 180. The controller 180 can calculate the swaying time. If the controller 180 determines that the display device 100a is sways over 5 seconds, the controller 180 can switch the displayed analog watch screen to the digital watch screen. For instance, the controller 180 can set an event occurrence condition based on information such as a display device swaying time, a display device swaying strength, a display device swaying direction, a display device swaying count, a display device swaying speed and the like.

The sensing unit 140 can detect the state information of the user. The state information of the user may include a BPM (beats per minute), a body temperature, brain waves and the like. For instance, the sensing unit 140 detects a BPM (beats per minute) of the user and can then deliver it to the controller 180. If the delivered BPM (beats per minute) becomes equal to or greater than a predetermined count, the controller 180 can switch the analog watch screen to the digital watch screen.

Based on at least one of an input user command, a received data, a detected motion information of the display device and a detected state information of the user, the controller 180 can determine whether a preset condition is met. If the preset condition is met, the controller 180 can switch the analog watch screen to the digital watch screen. For instance, if the controller 180 receives data from a counterpart, the controller 180 can switch the analog watch screen to the digital watch screen. If the number of data received from a counterpart becomes equal to or greater than a predetermined number, the controller 180 can switch the analog watch screen to the digital watch screen. If the controller 180 receives an input of a touch gesture applied to a specific region of the displayed analog watch screen or an input of a touch gesture applied to an icon indicating the received data, the controller 180 can switch the analog watch screen to the digital watch screen.

If the display device 100a sways with a strength equal to or greater than a preset strength or a BPM (beats per minute) equal to or greater than a preset count is detected, the controller 180 can switch the analog watch screen to the digital watch screen. If a preset time remains until an input alarm time or an input appointment time, the controller 180 can switch the analog watch screen to the digital watch screen. If an input alarm time or an input appointment time arrives, the controller 180 can switch the analog watch screen to the digital watch screen. Further, the display device 100a can other output means such as vibration, sound, flickering light and the like simultaneously.

Figure 4:
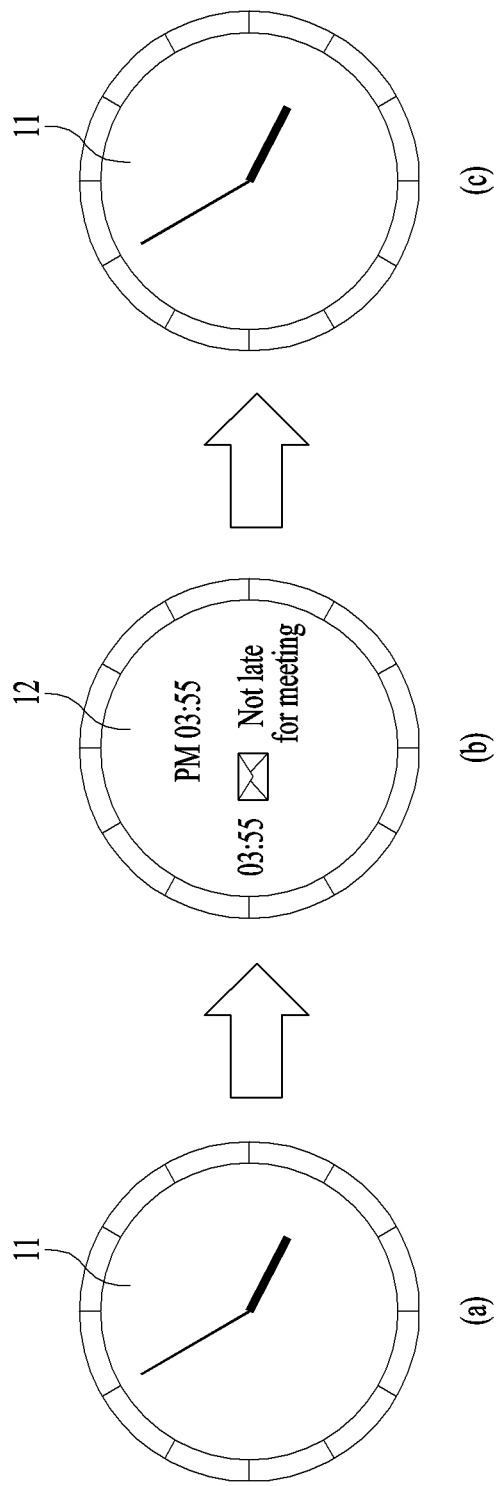
FIG. 4 is a diagram illustrating a switching operation between an analog watch screen and a digital watch screen according to one embodiment of the present invention.

So far, the configuration of the display device 100a is described. Various embodiments of the display device 100a are described as follows. FIG. 4 is a diagram illustrating a switching operation between an analog watch screen and a digital watch screen according to one embodiment of the present invention.

Referring to FIG. 4 (*a*), an analog watch screen 11 is illustrated. A display device can display the analog watch screen 11. In particular, the analog watch screen 11 can display images of a hour hand a minute hand. In some cases, the display device can include a physical hour hand and a physical minute hand. If the display device includes the physical hands, the display device can display scales or numerals indicating a time on the display unit. And, the display device can display a current time on the analog watch screen.

Referring to FIG. 4 (*b*), a digital watch screen 12 switched from the analog watch screen 11 is illustrated. According to one embodiment, the display device can be set to switch the analog watch screen to the digital watch screen if receiving data from an external device. In this instance, the digital watch screen may include a time information, an information on the received data and the like. For example, the display device can display a current time, a data reception time, an icon indicating a type of the received data, a partial content of the received data and the like.

Referring to FIG. 4 (*c*), the analog watch screen switched from the digital watch screen 11 is illustrated. If the display device receives an input of a touch gesture for selecting a displayed data, the display device can display detailed information on the selected data. For instance, if the display device receives a command for selecting a received text, the display device can display the whole contents of the received text. After the display device has displayed the detailed information on the selected data, if a predetermined time expires or an additional input is not applied for a predetermined time, the display device can switch to the analog watch screen 11.

The display device can not receive an input of another command through the digital watch screen 12 shown in FIG. 4 (*b*). Hence, if a predetermined time expires or an input is not applied for a predetermined time, the display device can switch the digital watch screen 12 to the analog watch screen 11.

Meanwhile, the display device can differentiate a standby time in accordance with a currently displayed screen until switching to the analog watch screen 11. For one example, if the display device receives an input of a selection command of a received text from a user and then displays the whole content of the received text, the display device stands by for 15 seconds and can then switch to the analog watch screen 11. Further, if the display device displays the digital watch screen 11 shown in FIG. 4 (*b*), the display device stands by for 5 seconds and can then switch to the analog watch screen 11.

Figure 5:
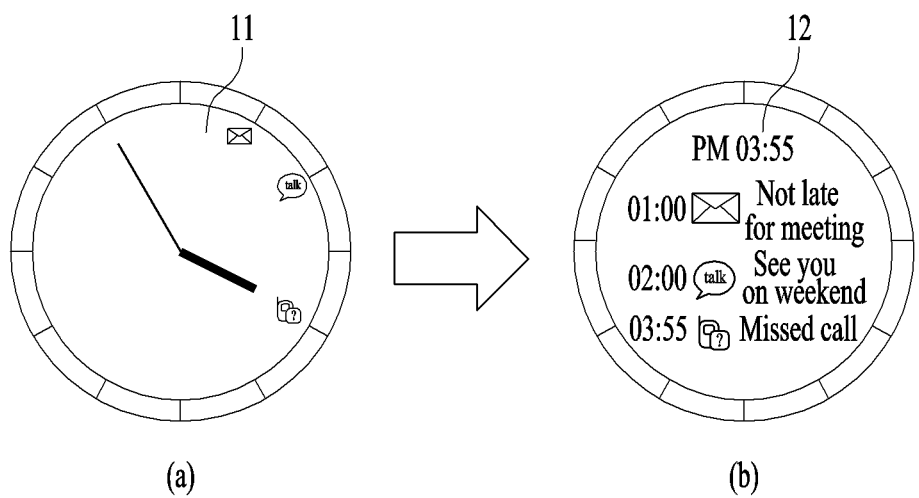
FIG. 5 is a diagram illustrating a first embodiment of switching an analog watch screen to a digital watch screen.

FIG. 5 is a diagram illustrating a first embodiment of switching an analog watch screen to a digital watch screen. Referring to FIG. 5 (*a*), an analog watch screen 11 on which icons are related to the received data are displayed is illustrated. When the display device receives the preset number of data, the display device can switch to a digital watch screen 12. Hence, if the number of the received data is smaller than the preset number, the display device can maintain the analog watch screen 11.

If the display device receives data, the display device can display an icon related to the received data on a region of the analog watch screen 11 corresponding to a reception time of the data. For instance, if the display device receives an SMS around 1 o'clock, a talk message around 4 o'clock and a missed call around 4 o'clock, the display device can display an SMS icon, a talk icon and a missed call icon on a region corresponding to 1 o'clock, a region corresponding to 2 o'clock and a region corresponding to 4 o'clock, respectively. In particular, the display device can display the icon related to the received data on a location, which is mapped to the reception time, of the analog watch screen.

Meanwhile, the display device can display an icon, which is related to data failing to be checked by a user, on the analog watch screen 11 only. For instance, as an incoming call was received around 3 o'clock, if a user speaks to a counterpart, the display device can not display an icon related to the incoming call received around 3 o'clock. As an SMS message was received around 3 o'clock, if a user checks the received SMS message received around 3 o'clock, the display device can not display an icon related to the SMS message received around 3 o'clock.

Referring to FIG. 5 (*b*), a digital watch screen 12 switched from the analog watch screen 11 is illustrated. When the display device receives a plurality of data, the display device can switch the analog watch screen 11 to the digital watch screen 12. In particular, if a preset number of data are received from an external device, the display device can switch the analog watch screen 11 to the digital watch screen 12. For instance, if 3 data are received, the display device can switch the analog watch screen 11 to the digital watch screen 12. The display device switches to the digital watch screen 12 and can then display a time information, a data reception time, a type information of the received data, a summary information of the received data and the like.

If a preset number of unchecked data exist, the display device can switch to the digital watch screen 12. For instance, if 3 unchecked data exist, the display device can be set to switch to the digital watch screen. As the display device has received 5 data between 1 PM to 3 PM, a user can check 3 data. Hence, 2 data have been unchecked. If the display device receives 1 data at 3:55 PM, since 3 data are unchecked, the display device can switch to the digital watch screen 12.

If the display device receives an input of a command for selecting one data through the switched digital watch screen 12, the display device can display details of the selected data. For instance, if the display device receives a command for selecting a received SMS message, the display device can display the whole contents of the received SMS message. After the display device has displayed the detailed information on the selected data, if a predetermined time expires or an additional input is not applied for a predetermined time, the display device can switch to the analog watch screen 11 or the digital watch screen 12. The display device can not display the icon and reception information related to the SMS message checked by a user. Meanwhile, if a user does not check at least one received data, the display device can maintain the switched digital watch screen 12.

Figure 6:
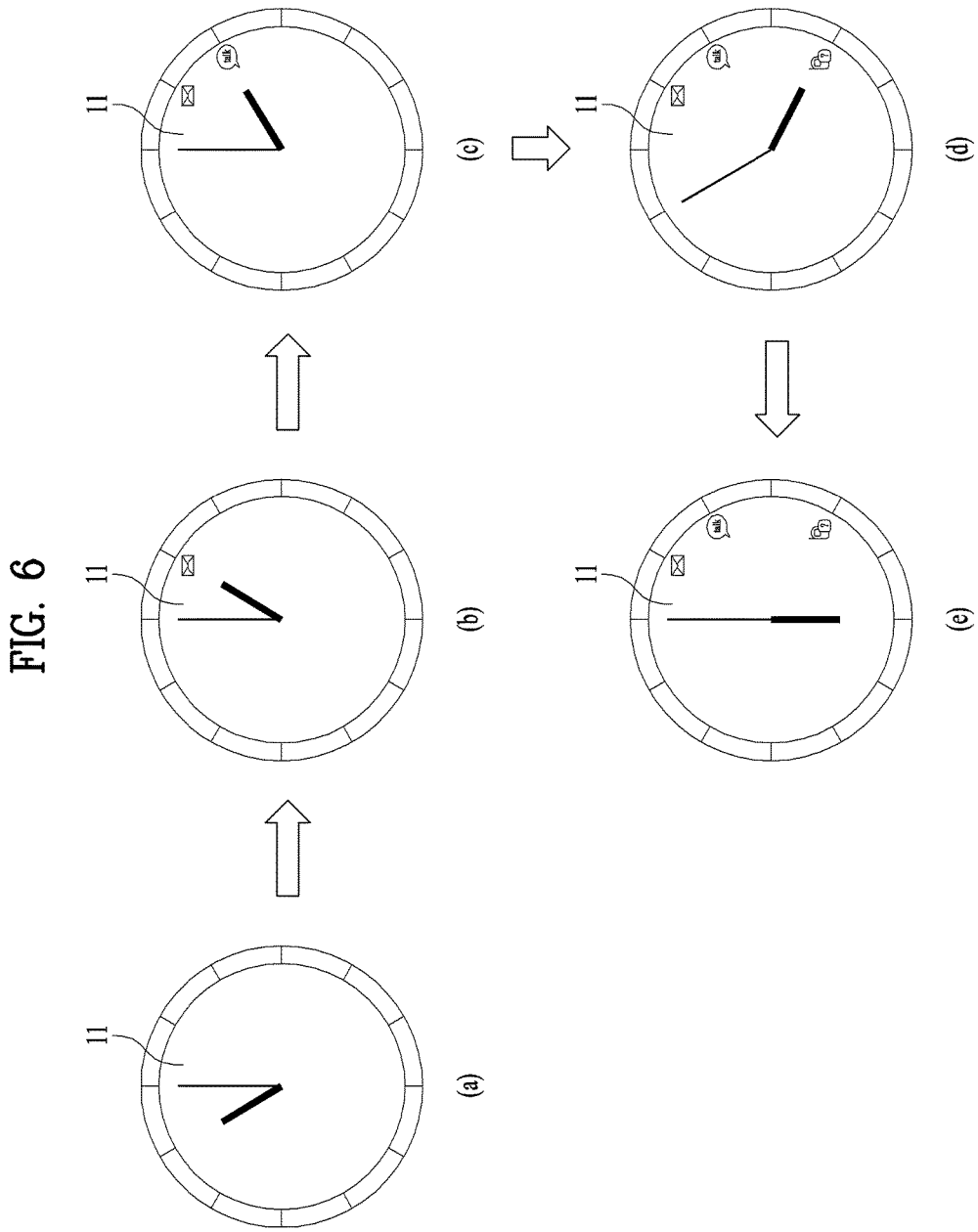
FIG. 6 is a diagram illustrating an event related UI displayed on an analog watch screen according to one embodiment of the present invention.

FIG. 6 is a diagram illustrating an event related UI displayed on an analog watch screen according to one embodiment of the present invention. Referring to FIG. 6 (a), an analog watch screen 11 is illustrated. As mentioned in the foregoing description, if the display device receives 1 data, the display device can switch the analog watch screen 11 to a digital watch screen 12. If the display device receives a preset data, the display device can switch to the digital watch screen 12. Yet, although the display device receives data for a time set as a screen switching prohibited time, the display device does not switch to the digital watch screen 12.

In particular, if the display device receives data from an external device for a time set as a screen switching prohibited time, the display device can maintain the analog watch screen instead of switching to the digital watch screen. For instance, the sleep hour may include a time randomly set by a user. For instance, a user can set a sleep hour to a period between 11 PM to 6 AM. The display device can set a sleep hour to a period between a user's sleep start time and a user's sleep end time by determining a presence or non-presence of a user's sleep based on a detected user's state information. For one example, in the display device shown in FIG. 6, a sleep hour is set to a period between 11 PM and 6 AM.

Referring to FIG. 6 (b), the analog watch screen 11 having an SMS icon displayed thereon is illustrated. As mentioned in the foregoing description, the display device does not switch to the digital watch screen 12 despite receiving data for the switching prohibited time. And, the display device can display an icon related to a received data on the analog watch screen 11. In particular, the display device can display the icon related to the received data at a location on the analog watch screen 11 mapped to a reception time. For instance, the display device can receive an SMS message from a counterpart around 1 AM. If so, the display device can display an SMS icon at a location of '1 o'clock' on the analog watch screen 11 corresponding to a reception time of the SMS message without switching to the digital watch screen 12.

Referring to FIG. 6 (c), the analog watch screen 11 having a talk icon displayed thereon is illustrated. The display device can receive a talk message around 2 o'clock. Hence, the display device can display the talk icon at a location of '2 o'clock' on the analog watch screen 11 corresponding to a repletion time of the talk message. Since a previously received SMS message is unchecked yet, the display device can display both of the SMS icon and the talk icon.

Referring to FIG. 6 (d), the analog watch screen 11 having a missed call icon displayed thereon is illustrated. The display device can receive an incoming call around 4 o'clock. Yet, a user may not receive the incoming call. Hence, the display device can display the missed call icon at a location of '4 o'clock' on the analog watch screen 11 corresponding to a reception time of the incoming call. The display device can display the SMS icon and the talk icon together with the missed call icon.

Referring to FIG. 6 (e), the analog watch screen 11 indicating 6 o'clock is illustrated. In FIG. 6, a time between 11 PM and 6 AM is set as a sleep hour. Hence, a switching prohibited time ends at 6 AM. If the switching prohibited time ends, the display device can output a notification signal. For instance, the display device can output vibration, sound and/or the like. Moreover, if the switching prohibited time ends, the display device can switch the analog watch screen 11 to the digital watch screen 12.

Figure 7:
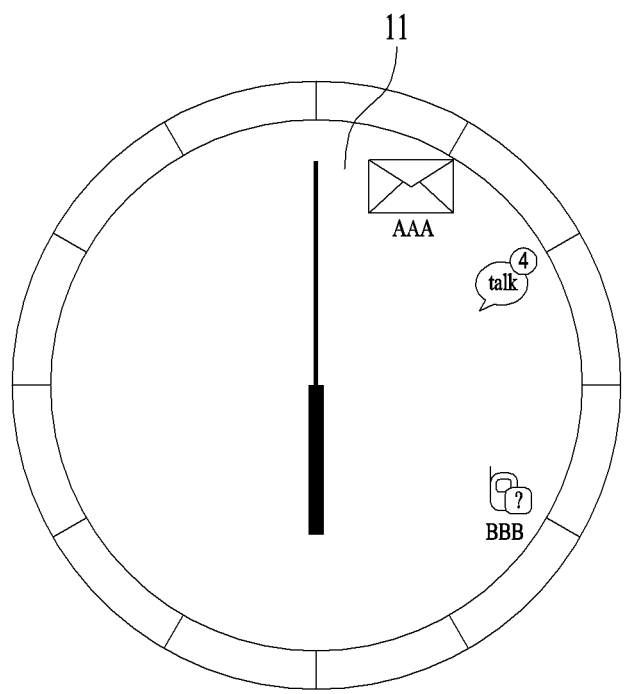
FIG. 7 is a diagram illustrating another embodiment of an event related UI displayed on an analog watch screen.

FIG. 7 is a diagram illustrating another embodiment of an event related UI displayed on an analog watch screen. Referring to FIG. 7, as mentioned in the foregoing description, if the switching prohibited time is set, the display device does not switch to the digital watch screen 12. If data is received from an external device, the display device can display an icon related to the received data on a region of the analog watch screen 11 corresponding to a reception time. In particular, the display device can display the icon related to the received data at a location on the analog watch screen 11 mapped to the reception time.

Meanwhile, the display device can display a received data icon on the analog watch screen 11 in various ways. For instance, the display device can control a sender information to be additionally displayed on the received data icon. Referring to FIG. 7, if an SMS message is received from AAA around 1 o'clock, the display device can display the sender 'AAA' at a location corresponding to 1 o'clock together with an SMS icon. If an incoming call is received from BBB around 4 o'clock, the display device can display a missed call icon at a location corresponding to 4 o'clock together with the sender 'BBB'.

The display device can receive a plurality of data during a prescribed period of time. The display device can display the total number of the received data as well. If 4 talk messages are received around 2 o'clock, as shown in FIG. 7, the display device can display a numeral indicating 4 at a location corresponding to 2 o'clock together with a talk icon. If the 4 talk messages are received from the same user, the display device can display the information on a corresponding sender as well.

The display device can also control icons to be displayed in different sizes depending on preset importance significances, respectively. Referring to FIG. 7, the SMS icon received around 1 o'clock is displayed in a size relatively larger than those of other icons. The display device can control significant data to be displayed by being distinguished from each other using colors, special effects and the like. In this instance, the significant data may mean the data received from a user classified as a significant counterpart within the display device. Moreover, the significant data may mean the data to which a setting value indicating significance is attached when a counterpart sends the data.

Figure 8:
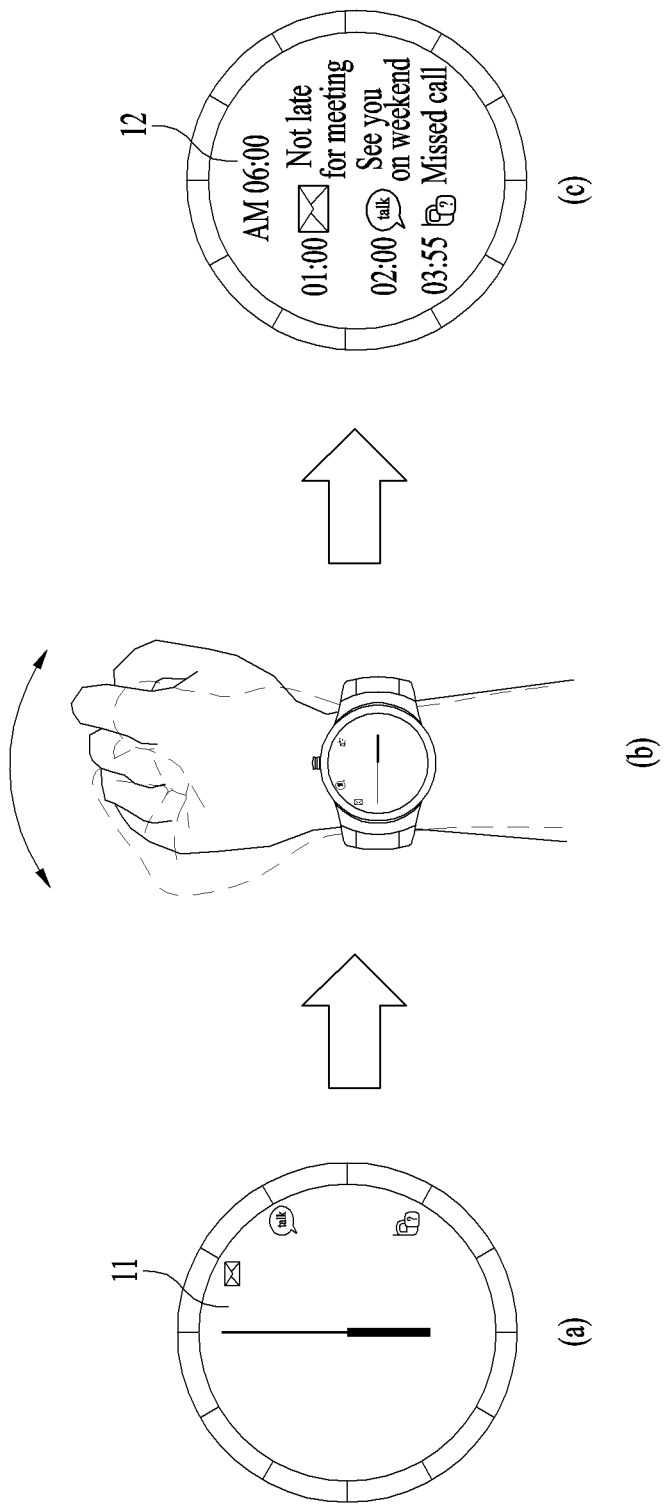
FIG. 8 is a diagram illustrating a second embodiment of switching an analog watch screen to a digital watch screen.

Next, FIG. 8 is a diagram illustrating a second embodiment of switching an analog watch screen to a digital watch screen. Referring to FIG. 8 (a), an analog watch screen 11 on which an icon meaning a received data is displayed is illustrated. As mentioned in the foregoing description, although the display device receives data, if a switching prohibited time is set, the digital device does not switch to a digital watch screen 12. The digital device may not set a data reception event as a digital watch screen switch event. The display device can set a sway of the display device as a digital watch screen switch event.

Referring to FIG. 8 (b), a display device currently swaying over a preset value is illustrated. If the display device sways over a predetermined value, the display device can switch an analog watch screen 11 to a digital watch screen 12. According to one embodiment, the display device can set a digital watch screen switch event with reference to strength, distance, count, time and/or the like. For instance, if the display device sways over a preset strength, the display device can switch to the digital watch screen 12. For instance, if the display device is moved over a preset distance, the display device can switch to the digital watch screen 12. For instance, if the display device sways over a preset count, the display device can switch to the digital watch screen 12. For instance, if the display device sways over a preset time, the display device can switch to the digital watch screen 12. For instance, the display device can set up a digital watch screen switch event by combining at least two or more conditions together.

Referring to FIG. 8 (c), the digital watch screen 12 switched from the analog watch screen 11 is illustrated. If a preset condition is met, the display device can switch the analog watch screen 11 to the digital watch screen 12. The digital watch screen 12 may include a current time, a reception time of data, a type information of a received data, a summary information of a received data and the like. If a prescribed data is selected, the display device can display details of the selected data.

Figure 9:
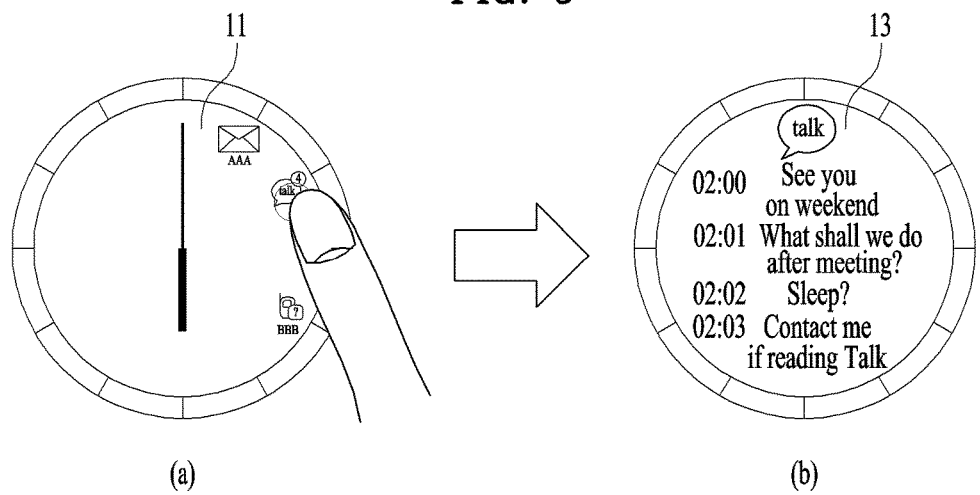
FIG. 9 is a diagram illustrating a third embodiment of switching an analog watch screen to a digital watch screen.

FIG. 9 is a diagram illustrating a third embodiment of switching an analog watch screen to a digital watch screen. Referring to FIG. 9 (a), an analog watch screen 11 on which an icon indicating a received data is displayed is illustrated. The display device can display an icon associated with the received data on the analog watch screen 11. The display device can display the icon on a region corresponding to a reception time of the data. For instance, if an SMS message is received around 1 o'clock, an SMS related icon can be displayed on a region of the analog watch screen 11 corresponding to 1 o'clock. If a talk message is received around 2 o'clock, a talk message related icon can be displayed on a region of the analog watch screen 11 corresponding to 2 o'clock. If a missed call is received around 4 o'clock, a missed call related icon can be displayed on a region of the analog watch screen 11 corresponding to 4 o'clock. If a command for selecting a displayed icon is input, the display device can display data related to the selected icon.

Referring to FIG. 9 (b), a talk message displayed screen 13 is illustrated. Since the display device receives an input of a command for selecting an icon related to a talk message, the display device can display the talk message. In particular, if the icon displayed on the analog watch screen 11 is selected, the display device can display contents of the received data. In addition, the talk message may include a reception time and content. The screen 13 shown in FIG. 9 (b) is a talk application launched screen. Yet, the display device can display the talk message by launching the talk application or by display a digital watch screen. In this instance, the digital watch screen may include a current time and details of the received data.

Figure 10:
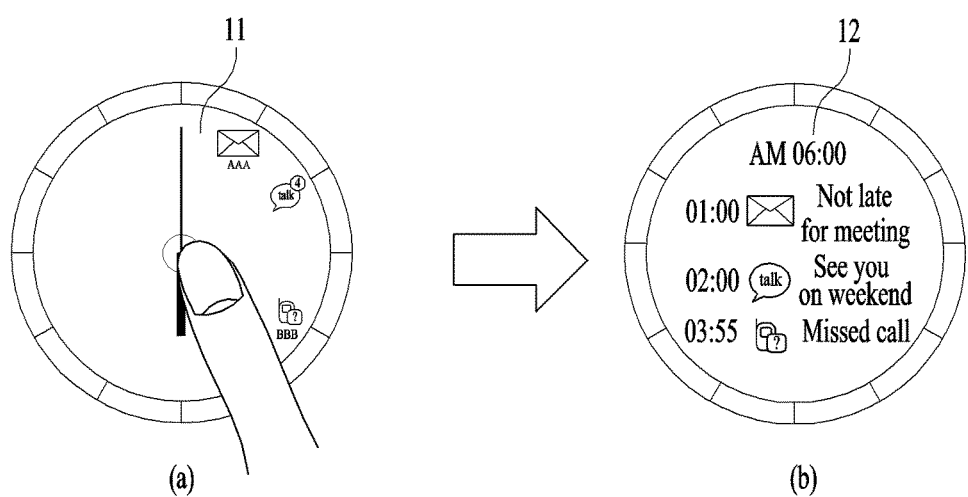
FIG. 10 is a diagram illustrating a fourth embodiment of switching an analog watch screen to a digital watch screen.

Next, FIG. 10 is a diagram illustrating a fourth embodiment of switching an analog watch screen to a digital watch screen. Referring to FIG. 10 (a), an analog watch screen 11 on which an icon meaning a received data is displayed is illustrated. A setting for switching to a digital watch screen 12 of the display device can be set to deactivation. The display device can also be set to a switching prohibited time, and not receive data amounting to a set number. Hence, the display device can maintain the analog watch screen 11 despite receiving the data. If the display device receives an input of a touch gesture applied to a preset region, the display device can switch to the digital watch screen 12. For instance, the preset region may include a central region of the analog watch screen 11. If the display device receives an input of a preset touch gesture, the display device can switch the analog watch screen 11 to the digital watch screen 12. For instance, the preset touch gesture may include a sweep gesture of moving in a specific direction by maintaining a corresponding touch.

Referring to FIG. 10 (b), the digital watch screen 12 switched from the analog watch screen 11 is illustrated. The display device can display a current time and information on a received data. For instance, the display device can display a data received time, a type information of a received data, an initial portion of a text of the received data and the like. If the data information displayed on the digital watch screen 12 is selected, the display device can display a detailed information of the selected data. In particular, the display device can recognize an input of a touch gesture applied to a preset region as a command for switching to the digital watch screen 12.

So far, the embodiments for switching the analog watch screen 11 to the digital watch screen 12 are described. In the following description, one embodiment for displaying both of the analog watch screen 11 and the digital watch screen 12 simultaneously is described. In particular, FIG. 11 is a diagram illustrating one embodiment of displaying an analog watch screen and a digital watch screen simultaneously.

Figure 11:
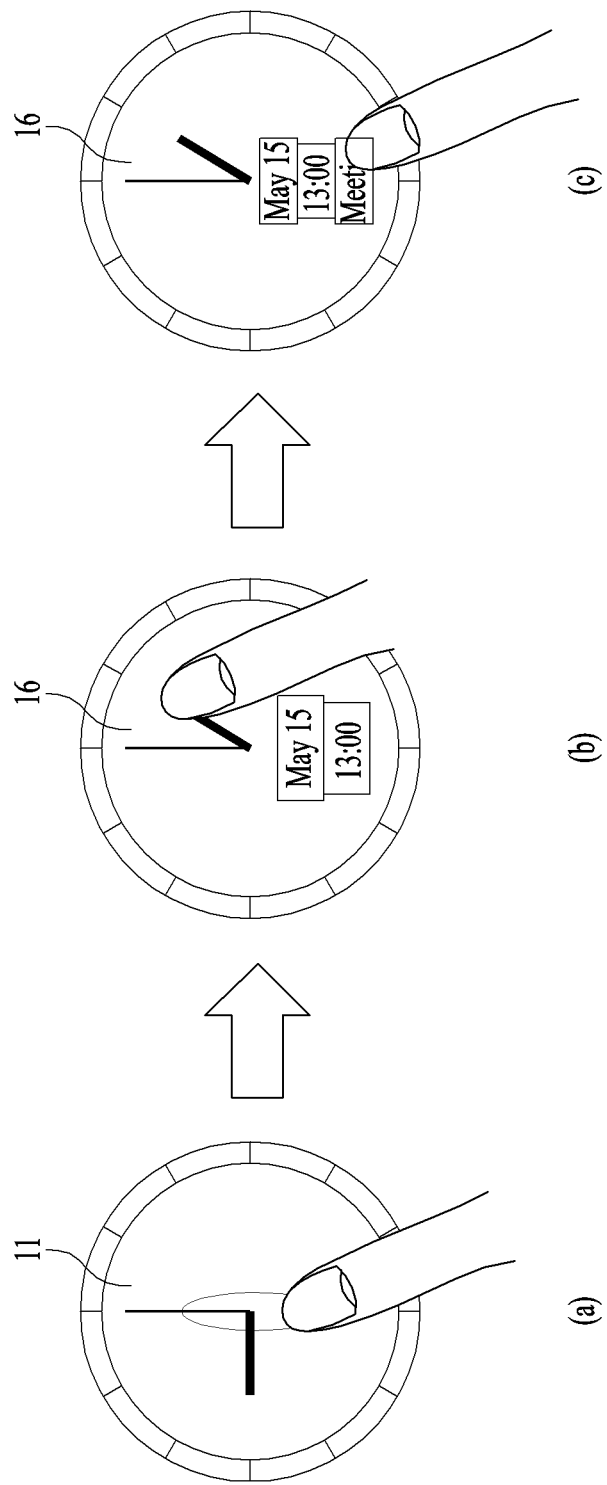
FIG. 11 is a diagram illustrating one embodiment of displaying an analog watch screen and a digital watch screen simultaneously.

Referring to FIG. 11 (a), an analog watch screen 11 is illustrated. An alarm or schedule can be set in the display device. First of all, the display device can receive an input of a preset touch gesture through the analog watch screen 11. According to one embodiment, the preset touch gesture may include a sweep gesture of moving in a specific direction by maintaining a touch. If the display device receives an input of the preset touch gesture, the display device can display an alarm setting screen.

Referring to FIG. 11 (b), an alarm setting screen 16 is illustrated. The display device can display a region to which a time can be input. When the display device displays the time input region initially, a current hour or time can be displayed by the display device. For instance, if a current time is 9 AM, May 10, May 10 09)00 can be displayed. The display device can receive an input of a text through the time input region. For instance, if an appointment time is 1 PM, May 15, a user can set an alarm by directly inputting 'May 15, 13:00' to the time input region. The display device can receive an input of time using rotations of watch hands. In particular, a user can touch to move an hour hand of a watch to a location corresponding to 1 PM. And, the user can touch to move a minute hand of the watch to a location corresponding to 00 minutes. The display device can set an alarm time to a time indicated by the movements of the hour and minute hands. Meanwhile, the display device can receive an input of a date with a text irrespective of an alarm time setting method.

Referring to FIG. 11 (c), the alarm setting screen 16 including an input window for inputting a memo is illustrated. The display device can set an alarm time by a direct user input or rotations of watch hands. If an alarm time setting is completed, the display device can display the memo input window. And, the display device can receive an input of a memo with a text. The alarm time set display device can output a notification ahead of a preset time from the alarm time in advance.

Figure 12:
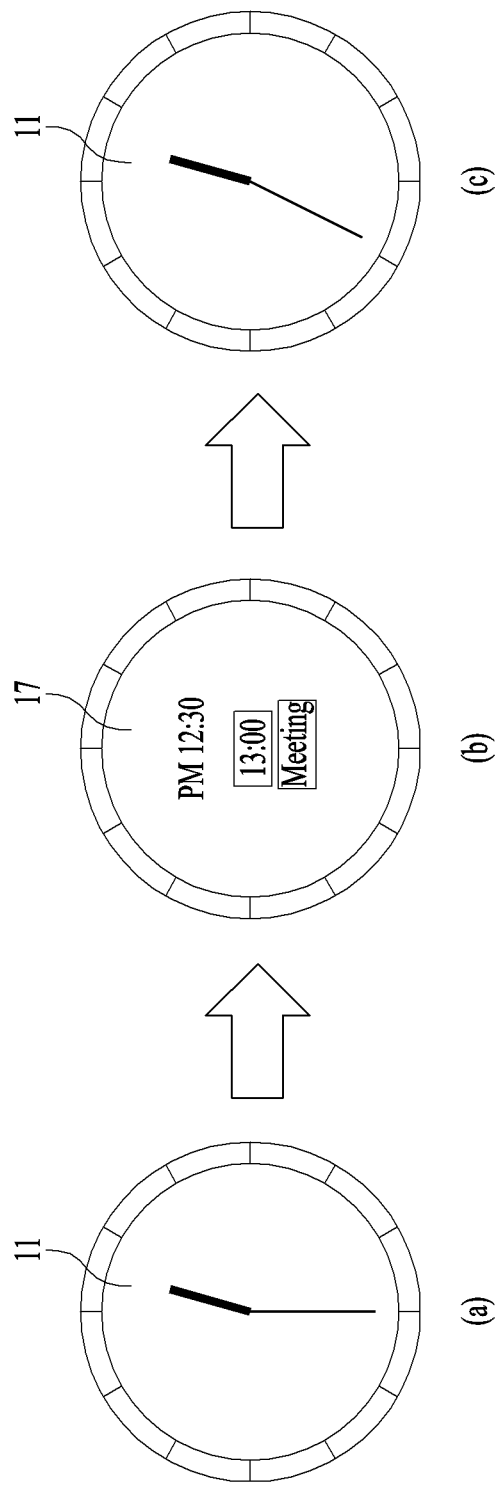
FIG. 12 is a diagram illustrating a fifth embodiment of switching an analog watch screen to a digital watch screen.

FIG. 12 is a diagram illustrating a fifth embodiment of switching an analog watch screen to a digital watch screen. Referring to FIG. 12 (a), an analog watch screen 11 is illustrated. A meeting alarm is set for 1 PM in the display device shown in FIG. 12. In addition, an advance notification is set for 30 minutes in advance. The display device can display a current time on the analog watch screen 11. In this instance, the current time is 12:30 PM.

Referring to FIG. 12 (b), a digital watch screen 17 switched from the analog watch screen 11 is illustrated. As mentioned in the foregoing description, an alarm and an advance notification may be set in the display device. Since the alarm is set for 1 PM and the advance notification is set for 30 minutes in advance, the display device can launch an advance notification function at 12:20 PM. The display device can switch the analog watch screen 11 to the digital watch screen 17. Further, the display device can display the current time '12:30 PM', the set alarm time and the memo. When the display device launches the advance notification, the display device can output a notification sound or an indicator displayed by turning on and off light of a screen together. The indicator may be output for a predetermined period of time only or keep being output during a notification sustained time.

Referring to FIG. 12 (c), the analog watch screen 11 switched from the digital watch screen 17 is illustrated. The display device can set up a sustained time of an advance notification. According to one embodiment, the display device can set the sustained time of the advance notification to one of 10 seconds, 1 minute, 5 minutes and the like. For instance, if the sustained time of the advance notification is set to 5 minutes, the display device switches the analog watch screen 11 to the digital watch screen 17, maintains the digital watch screen 17 for 5 minutes, and can then switch the digital watch screen 17 to the analog watch screen 11 again.

Meanwhile, if the display device receives an input of an advance notification end gesture through the digital watch screen 17, the display device ends the advance notification immediately and can then switch to the analog watch screen 11. For instance, the advance notification end gesture may include a touch gesture of a specific type or a gesture of swaying the display device over a preset strength, sped or count.

Figure 13:
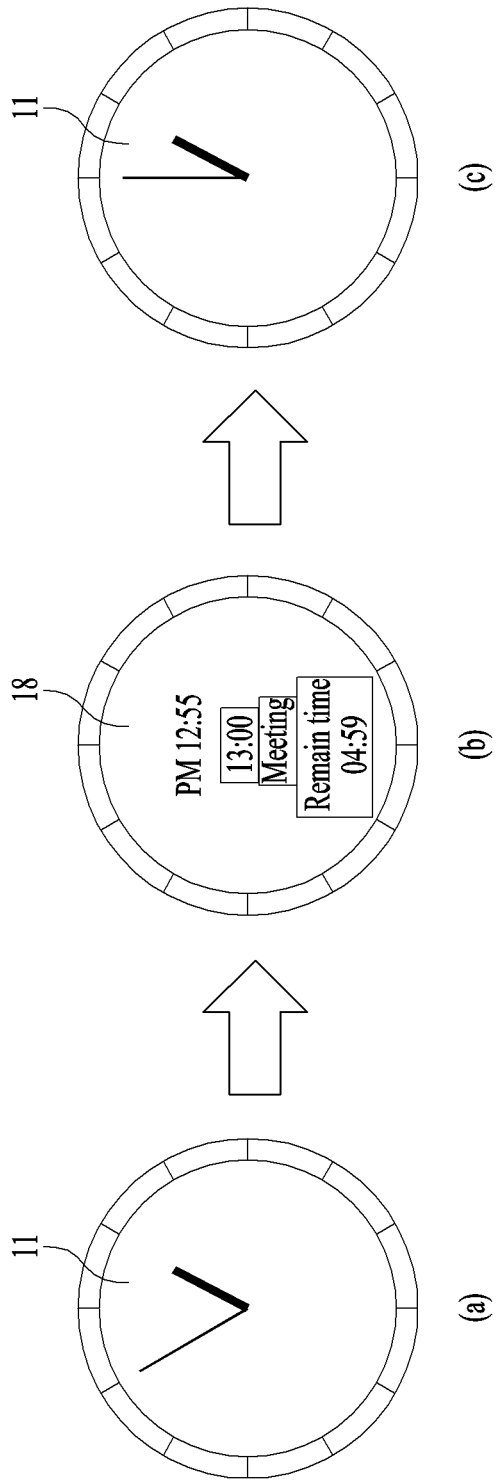
FIG. 13 is a diagram illustrating a sixth embodiment of switching an analog watch screen to a digital watch screen.

Next, FIG. 13 is a diagram illustrating a sixth embodiment of switching an analog watch screen to a digital watch screen. Referring to FIG. 13 (a), an analog watch screen 11 is illustrated. As mentioned in the foregoing description, the display device has an alarm set for 1 PM. And, the display device can launch an advance notification function before 30 minutes from an alarm time. Moreover, the display device can further launch a second advance notification function.

Referring to FIG. 13 (b), the display device currently launching the second advance notification function is illustrated. The display device can be set to launch the second advance notification function before 5 minutes from the alarm time. Since the display device has the alarm set for 1 PM, the display device can launch the second advance notification function at 12:55 PM. If it is 12:55 PM, the display device can switch the analog watch screen 11 to a digital watch screen 18. The display device can display a current time and information on the set alarm.

In particular, when the display device launches the second advance notification function before 5 minutes from the alarm time, the display device can also display a countdown information on the 1-second countdown from the 5 minutes before the alarm time. As soon as the second advance notification function is launched, the display device can also output a notification sound or an indicator of a type of turning on and off the light of the screen. If the alarm time arrives, the display device can output an alarm sound.

Referring to FIG. 13 (c), the analog watch screen 11 switched from the digital watch screen 18 is illustrated. If the alarm time arrives, the display device outputs a notification sound and can switch to the analog watch screen 11. In particular, if an input alarm time matches an actual time, the display device can switch the digital watch screen 18 to the analog watch screen 11. Meanwhile, the display device can include a digital watch screen of plural steps according to an embodiment.

Figure 14:
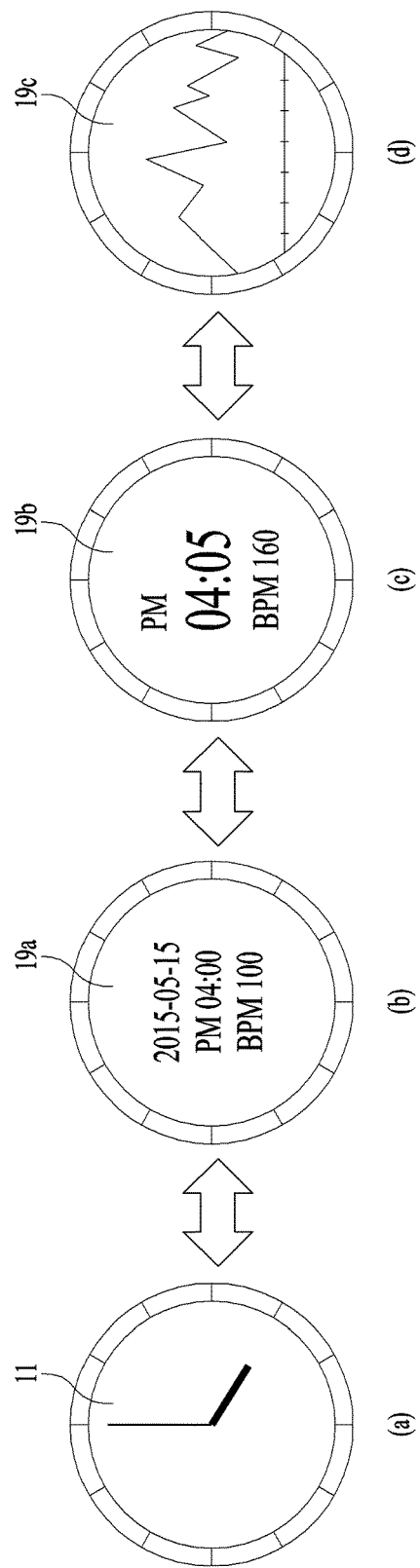
FIG. 14 is a diagram illustrating a display device including a digital watch screen of plural steps according to one embodiment of the present invention.

FIG. 14 is a diagram illustrating a display device including a digital watch screen of plural steps according to one embodiment of the present invention. Referring to FIG. 14 (a), an analog watch screen 11 is illustrated. The display device can normally display the analog watch screen 11. Further, the display device can detect a user's state information (e.g., biometric state information, etc.). According to one embodiment, the user's state information may include at least one of a BPM (beats per minute), a body temperature, a respiration rate, a blood pressure and the like. Based on the detected user's state information, the display device can switch a displayed screen.

Referring to FIG. 14 (b), a digital watch screen 19a on which information in a first size is displayed is illustrated. If a state information equal to or greater than a preset first size is detected, the display device can switch the analog watch screen 11 to a digital watch screen 19a. In this instance, the digital watch screen 19a switched from the analog watch screen 11 can display the information in the first size. According to one embodiment, the user's state information may include a BPM (beats per minute) and the displayed information may include a current date, a current hour, a BPM (beats per minute), and the like.

The display device can also display a graph of at least one information currently detected as well. For instance, if a user is currently running, the display device can detect a running time, a running distance, the number of steps, a BPM (beats per minute), a body temperature, a blood pressure and the like. The display device can display a graph of the detected at least one information. According to one embodiment, the display device can display a BPM (beats per minute) graph only. Alternatively, the display device can display a running distance, a running time and a BPM (beats per minute) alternately.

The display device can detect a state information equal to or greater than a second size that is greater than the first size. Meanwhile, if the display device detects a state information smaller than the first size, the display device can switched to the analog watch screen 11 again. Referring to FIG. 14 (c), a digital watch screen 19b displayed in the second size is illustrated. If the display device detects the state information equal to or greater than the second size, the display device can display the information displayed on the digital watch screen 19b in a greater size. In some cases, the display device can not display the information displayed in first size in part.

According to one embodiment, the display device displays a current time in a larger size and can also display a BPM (beats per minute). The current date used to be displayed on the digital watch screen 19a in the first size may not be displayed. For instance, the display device can include a wearable watch. In particular, the wearable device can display the analog watch screen 11. A user can exercise by wearing the wearable device. If the user keeps exercising, a BPM (beats per minute) of the user may increase. Further, the wearable watch can detect the BPM (beats per minute) of the user.

If the detected BPM (beats per minute) becomes equal to or greater than a first count, the wearable watch can switch to the digital watch screen 19a displayed in the first size. The user may continue to perform the exercise. If the wearable watch detects a BPM (beats per minute) equal to or greater than a preset second count greater than the first count, the wearable watch can switch to the digital watch screen 19b displayed in the second size larger than the first size. Moreover, as mentioned in the foregoing description, the display device can display a graph of the currently detected at least one information as well.

The display device detects a sway and can then switch a screen. The display device can detect a strength or speed of the sway. If the display device detects the sway over a preset first strength or a preset first speed, the display device can switch to the digital watch screen 19a displayed in the first size. If the display device detects the sway over a second strength greater than the first strength or a second speed greater than the first speed, the display device can switch to the digital watch screen 19b displayed in the second size.

Meanwhile, if the display device detects a state information in a size smaller than the second size, the display device can switch to the digital watch screen 19a in the first size again. In particular, if the display device detects a sway in a range between the first strength and the second strength or a user's state information in a range between the first count and the second count, the display device can switch the digital watch screen 19b displaying the information in the second size to the digital watch screen 19a displaying the information in the first size. If the display device detects a sway with a strength smaller than the first strength or a user's state information smaller than the first count, the display device can switch the digital watch screen 19a displaying the information in the first size to the analog watch screen 11.

Referring to FIG. 14 (d), a graph displayed screen 19c is illustrated. If the display device detects a state information equal to or greater than a third size, the display device can display a screen 19c on which a graph is displayed only. The display device can detect an exercise time, an exercise distance, a moving time, a moving distance, the number of steps, a BPM (beats per minute), a body temperature, a blood pressure and the like. The display device can display the detected at least one information as a graph or may display graphs of a plurality of the information alternately. In some cases, the display device can display a current time digitally.

The display device can switch a screen by detecting a sway. The display device can detect a strength or speed of the sway. If the display device detects the sway over a preset third strength or a preset third speed, the display device can switch to the graph displayed screen 19c. So far, the embodiments for the switching between the analog watch screen and the digital watch screen are described. In the following description, embodiments for simultaneously displaying an analog watch screen and a digital watch screen are described.

Figure 15:
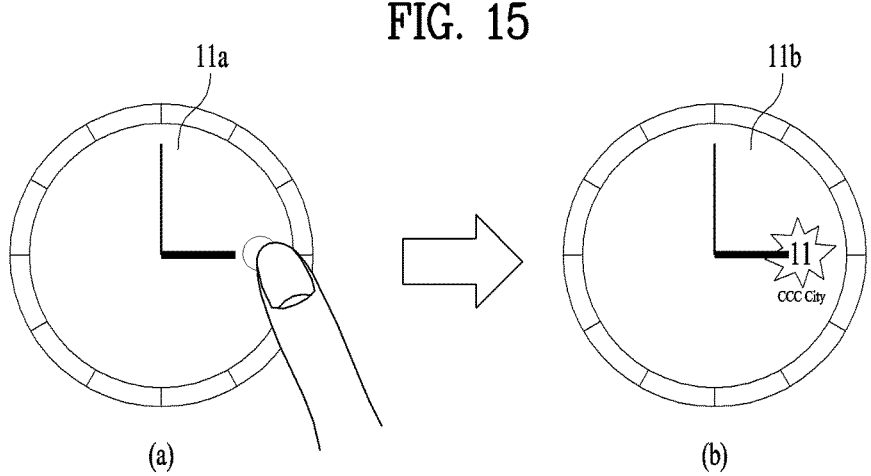
FIG. 15 is a diagram illustrating a process for displaying world time on an analog watch screen according to one embodiment of the present invention.

Next, FIG. 15 is a diagram illustrating a process for displaying world time on an analog watch screen according to one embodiment of the present invention. Referring to FIG. 15 (a), an analog watch screen 11a is illustrated. The display device can display the analog watch screen 11a including an hour hand and a minute hand. The display device can display a current time of a currently located region by communicating with a base station and/or the like, and can receive an input of a touch gesture applied to a tip region of the hour hand.

Referring to FIG. 15 (b), an analog watch screen 11b on which a time of another city is displayed is illustrated. In response to a user's touch gesture, the display device can display a time of another city. FIG. 15 (b) illustrates that a current time of a city CCC is 11 o'clock. In this instance, the displayed city can include a city set by a user. If a user is located overseas, the display device can display a time of a user's home town. The display device shown in FIG. 15 is displaying a time of a current location in analog form. Further, the display device is displaying a time of another city digitally. Hence, the display device can display the analog watch screen and the digital watch screen simultaneously.

Figure 16:
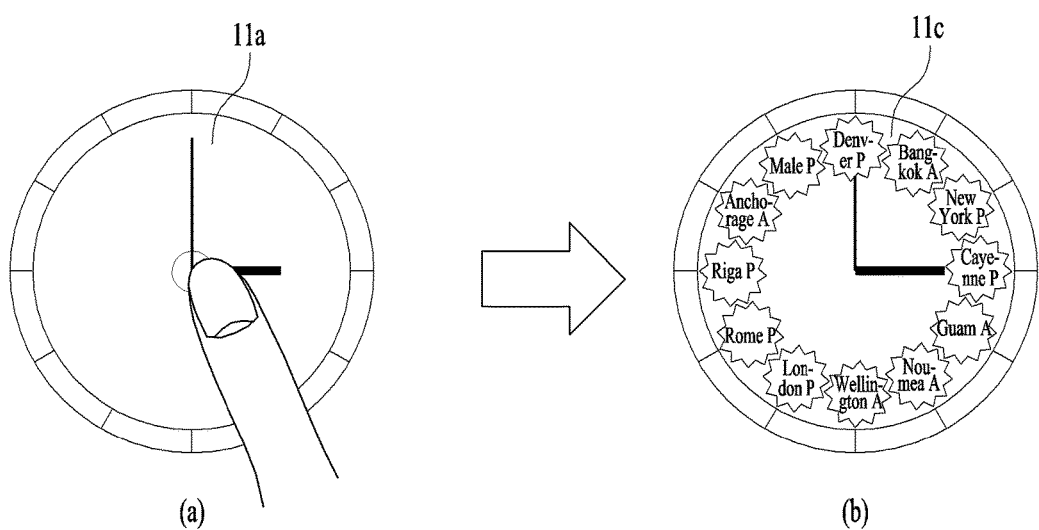
FIG. 16 is a diagram illustrating a process for displaying world time on an analog watch screen according to another embodiment of the present invention.

FIG. 16 is a diagram illustrating a process for displaying world time on an analog watch screen according to another embodiment of the present invention. Referring to FIG. 16 (a), an analog watch screen 11a is illustrated. The display device can display the analog watch screen 11a including an hour hand and a minute hand. The display device can display a current time of a currently located region by communicating with a base station and/or the like. The display device can receive an input of a touch gesture applied to a center region of the analog watch screen 11a.

Referring to FIG. 16 (b), an analog watch screen 11c on which times of a plurality of cities are is illustrated. In response to a user's touch gesture, the display device can display the time of another city. The display device displays a current time in analog form and can display a time of the city corresponding to each time region. According to one embodiment, if an area in which a user is currently located is Seoul at 3 AM, the display device can display 3 o'clock in analog form. Further, the display device can display the world time on each time region. For instance, since a current time in Denver is 12 PM, the display device can display 'Denver p', which means the city name and PM, on a 12 o'clock region.

In another instance, since a current time in Cayenne is 3 PM, the display device can display 'Cayenne p', which means the city name and PM, on a 3 o'clock region. In another instance, since a current time in Wellington is 6 AM, the display device can display 'Wellington A', which means the city name and AM, on a 6 o'clock region. Thus, the display device can display the times of the cities on the 1 o'clock region to the 12 o'clock region, respectively.

Figure 17:
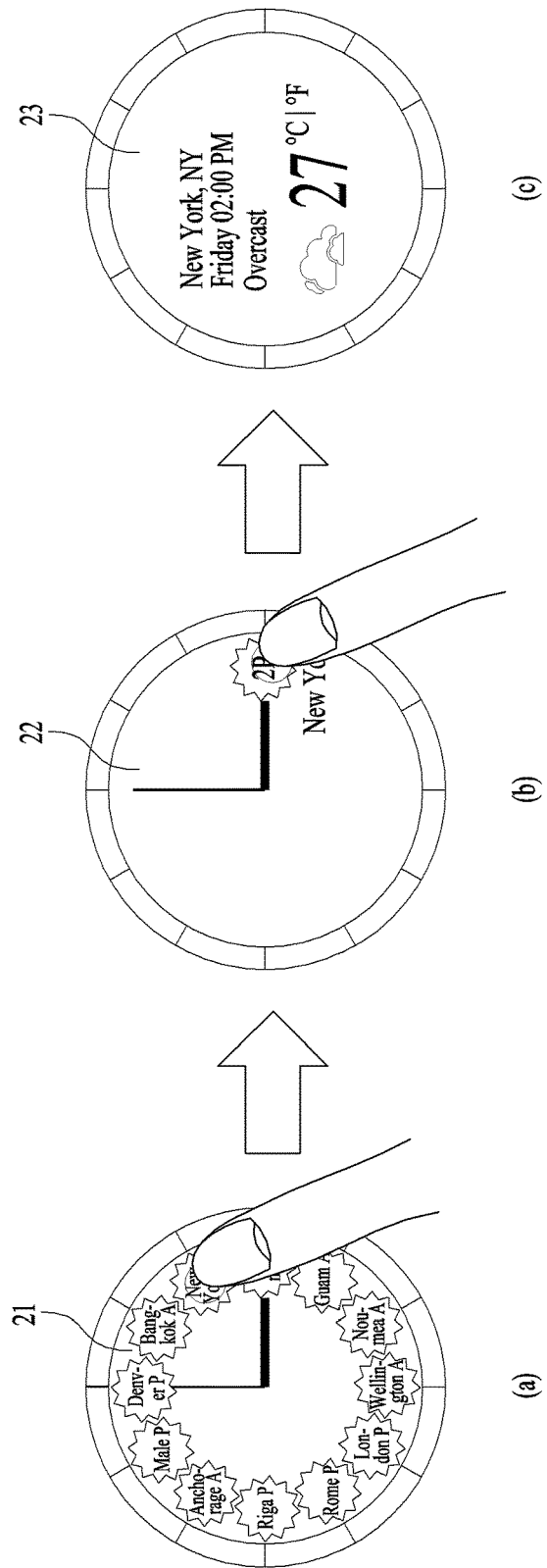
FIG. 17 is a diagram illustrating a process for displaying world time on an analog watch screen according to further embodiment of the present invention.

FIG. 17 is a diagram illustrating a process for displaying world time on an analog watch screen according to further embodiment of the present invention. Referring to FIG. 17 (a), an analog watch screen 21 on which cities and local times are displayed is illustrated. The display device can receive an input for selecting a prescribed city from a plurality of cities. If a user selects a prescribed city from the displayed cities, the selected city can be set as the city for displaying the time described with reference to FIG. 15.

If a plurality of cities exist in the same time region, the display device randomly displays a prescribed city and can display a numeral of the corresponding city. For instance, although 'Rome p' is displayed on a 7 o'clock region in FIG. 16 (b), if 4 more cities further exist, the display device can further display '4' together with 'Rome p'. If a user selects the region having 'Rome p' displayed thereon, the display device can display a list of cities existing on the same time zone. If the user selects a prescribed city from the displayed list, the selected city can be set as the city for displaying the time described with reference to FIG. 15.

Referring to FIG. 17 (b), an analog watch screen 22 on which the time of the selected city is displayed is illustrated. The display device displays a current time in analog form and can also display the selected city and a local time on a tip region of an hour hand. Referring to FIG. 17 (b), if a user selects New York, the display device can display the current time '3 AM' on the analog watch screen 22. And, the display device can display a time information on the selected city 'New York' on the tip portion of the hour hand. Hence, the display device can display '2 PM in New York' on a 3 o'clock region. The display device can receive an input of a user's selection command through the display city region.

Referring to FIG. 17 (c), a screen on which details of the selected city are displayed is illustrated. If the time displayed city is selected, the details of the selected city can be displayed. For instance, if the city is selected, weather information of the selected city can be displayed. The display device can display information on the city-related news, maps and the like as the details of the city. So far, various embodiments for the screen switching of the display device are described. In the following description, a flowchart for a display device control method is described in detail with reference to the accompanying drawing.

Figure 18:
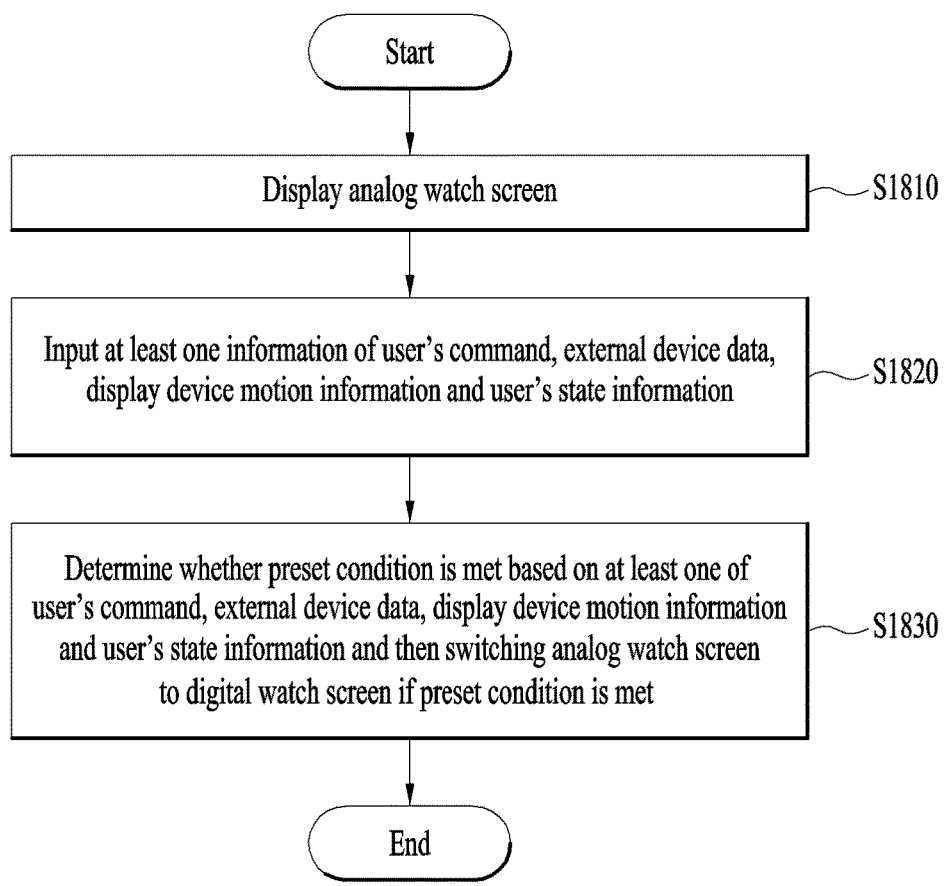
FIG. 18 is a flowchart of a display device controlling method according to one embodiment of the present invention.

FIG. 18 is a flowchart of a display device controlling method according to one embodiment of the present invention. Referring to FIG. 18, the display device displays an analog watch screen (S1810). In this instance, the analog watch screen may include an hour hand and a minute hand. In particular, the hour hand and the minute hand can be embodied as an image on the display unit. And, the analog watch screen can include scales or numerals to indicate hours and minutes. In some cases, the hour hand and the minute hand can be embodied with a physical means.

The display device receives an input of at least one information of a user's command, data of an external device, a motion information of the display device, a user's state information and the like (S1820). For instance, the user's command may include an alarm setting command. In particular, the user's command may include a command for outputting an alarm if a specific condition is met. The data of the external device may include a message, a call and the like. The motion information of the display device can include a sway information of the device. And, the user's state information may include such information as a BPM (beats per minute), a blood pressure, a respiration, a body temperature and the like.

Based on at least one of the user's command, the data of the external device, the motion information of the display device and the user's state information, the display device determines whether a preset condition is met. If the preset condition is met, the display device switches the analog watch screen to a digital watch screen (S1830). For instance, the preset condition may include at least one of an input of a preset number of data from an external device, a selection for an input data, a touch to a preset region, a sway of the display device over a preset strength, a match between an input alarm time and an actual time, a BPM (beats per minute) over a preset count, and the like. If a preset time expires or an additional input is not applied, the display device can switch the digital watch screen to the analog watch screen again.

Meanwhile, the display device can display the information in a first or second size on the digital watch screen depending on a detected strength and/or the like. For instance, if the display device sways over a first strength or a BPM (beats per minute) over a first count is detected, the display device can display the information in the preset first size by switching the analog watch screen to the digital watch screen. If the display device sways over a second strength greater than the first strength or a BPM (beats per minute) over a second count greater than the first count is detected, the display device can display the information in a second size greater than the first size. If the strength of the sway of the display device is lowered or the count of the BPM (beats per minute) is reduced, the display device can switch to the digital watch screen for displaying the information in the first size and the analog watch screen in turn.

Accordingly, embodiments of the present invention provide several advantages. First of all, according to at least one of embodiments of the present invention, if an event occurs, it is advantageous in that an analog watch screen is automatically switched to a digital watch screen. Secondly if a predetermined time expires and an additional input is not applied, it is advantageous in that a digital watch screen is automatically switched to an analog watch screen.

Thirdly, while a user is unable to check data, it is advantageous in that an analog watch screen is not switched to a digital watch screen. Fourthly, it is advantageous in that information related to an occurring event is displayed on a time region corresponding to an event occurrence time on an analog watch screen. Fifthly, it is advantageous in that a size of letters displayed on a digital watch screen can be displayed differently in response to sway of a display device.

The above-described methods can be implemented in a program recorded medium as computer-readable codes. The computer-readable media may include all kinds of recording devices in which data readable by a computer system are stored. The computer-readable media may include HDD (hard disk drive), SSD (solid state disk), SDD (silicon disk drive), ROM, RAM, CD-ROM, magnetic tapes, floppy discs, optical data storage devices, and the like for example and also include carrier-wave type implementations (e.g., transmission via Internet). Further, the computer may include the controller 180 of the terminal. It will be appreciated by those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:
1. A display device, comprising:
  a touch screen;
  a wireless communication unit configured to receive data from an external device;
  a sensing unit configured to sense at least one of a motion of the display device and biometric state information of a user; and a controller configured to:
   display an analog watch screen displaying a first number of icons related to the data received from the external device on the touch screen if a number of the data received from the external device is smaller than a predetermined number of data received from the external device, and
   switch the analog watch screen to a digital watch screen displaying a second number of icons related to the data received from the external device if the number of data received from the external device corresponds to the predetermined number of data, wherein the second number of icons in the digital watch screen includes the first number of icons in the analog watch screen,
   wherein each icon related to the data received from the external device is displayed together with a sender of the data at a location on the analog watch screen mapped to a reception time of the received data, and
   wherein each icon has a different size based on an importance of the sender.

2. The display device of claim 1, wherein the controller is further configured to switch the digital watch screen back to the analog watch screen in response to a preset time expiring or an additional input not being applied after the analog watch screen was switched to the digital watch screen.

3. The display device of claim 1, wherein the controller is further configured to display a content of the received data on the touch screen in response to a touch input on the displayed icon.

4. The display device of claim 1, wherein the controller is further configured to:
   set a switching prohibited time of the display device not to switch the analog watch screen to the digital watch screen for a preset time period, and
   maintain the analog watch screen without switching to the digital watch screen in response to the predetermined number of data received from the external device being received during the preset time period while the display device is set not to switch the analog watch screen to the digital watch screen.

5. The display device of claim 4, wherein the controller is further configured to set the switching prohibited time to a time between the user's sleep start time and the user's sleep end time by determining a presence or non-presence of the user's sleep based on the sensed biometric state information.

6. The display device of claim 1, wherein the controller is further configured to:
   display information in a preset first size by switching the analog watch screen to the digital watch screen, in response to the sensed motion of the display device indicating the display device sways over a first strength or the BPM is over a first count, and
   display the information in a second size larger than the first size in response to sensed motion of the display device indicating the display device sways over a second strength greater than the first strength or the BPM is over a second count greater than the first count.

7. The display device of claim 6, wherein the controller is further configured to:
   display the information in the first size on the digital watch screen having the information displayed in the second size thereon, in response to the sensed motion of the display device indicating the display device sways with a strength equal to or greater than the first strength and smaller than the second strength or the BPM is equal to or greater than the first count and smaller than the second count, and
   switch the digital watch screen to the analog watch screen in response to the sensed motion of the display device indicating the display device sways with the strength smaller than the first strength or the BPM is smaller than the first count is detected.

8. The display device of claim 1, wherein the controller is further configured to switch the analog watch screen to the digital watch screen in response to an input alarm time and an actual time.

9. The display device of claim 1, wherein the display device switches the analog watch screen to the digital watch screen in response to the predetermined touch input on the touch screen, when the predetermined touch input corresponds to one of a selection of an icon of the first number of icons related to the received data and a touch to a preset region of the touch screen.

10. The display device of claim 1, wherein the display device switches the analog watch screen to the digital watch screen in response to the specific motion of the display device, when the specific motion of the display device corresponds to a sway of the display device over a preset strength.

11. The display device of claim 1, wherein the display device switches the analog watch screen to the digital watch screen in response to the biometric state information of the user, when the biometric state information of the user corresponds to a sensing of a BPM (beats per minute) of the user over a preset count.

12. A method of controlling a display device, the method comprising:
   receiving, via a wireless communication unit of the display device, data from an external device;
   displaying, via a touch screen of the display device, an analog watch screen displaying a first number of icons related to the data received from the external device on the touch screen of the display device if a number of the data received from the external device is smaller than a predetermined number of data received from the external device;
   sensing, via a sensing unit of the display device, at least one of a motion of the display device and biometric state information of a user; and
   switching, via the controller of the display device, the analog watch screen to a digital watch screen displaying a second number of icons related to the data received from the external device if the number of data received from the external device corresponds to the predetermined number of data received from the external device, wherein the second number of icons in the digital watch screen includes the first number of icons in the analog watch screen,
   wherein each icon related to the data received from the external device is displayed together with a sender of the data at a location on the analog watch screen mapped to a reception time of the received data, and
   wherein each icon has a different size based on an importance of the sender.

13. The method of claim 12, further comprising:
   switching the digital watch screen back to the analog watch screen in response to a preset time expiring or an additional input not being applied after the analog watch screen was switched to the digital watch screen.

14. The method of claim 12, further comprising:
   displaying a content of the received data on the touch screen in response to a touch input on the displayed icon.

15. The method of claim 12, further comprising:

setting, via the controller, a switching prohibited time of the display device not to switch the analog watch screen to the digital watch screen for a preset time period;

maintaining, via the controller, the analog watch screen without switching to the digital watch screen in response to the predetermined number of data received from the external device being received during the preset time period while the display device is set not to switch the analog watch screen to the digital watch screen; and setting the switching prohibited time to a time between a sleep start time and a sleep end time of the user by determining a presence or non-presence of the user's sleep based on the detected sensed biometric state information.

16. The method of claim 12, further comprising:

displaying information in a preset first size by switching the analog watch screen to the digital watch screen, in response to the sensed motion of the display device indicating the display device sways over a first strength or the BPM is over a first count;

displaying the information in a second size larger than the first size in response to the sensed motion of the display device indicating the display device sways over a second strength greater than the first strength or the BPM is over a second count greater than the first count;

displaying the information in the first size on the digital watch screen having the information displayed in the second size thereon, in response to the sensed motion of the display device indicating the display device sways with a strength equal to or greater than the first strength and smaller than the second strength or the BPM is equal to or greater than the first count and smaller than the second count; and switching the digital watch screen to the analog watch screen in response to the sensed motion of the display device indicating the display device sways with the strength smaller than the first strength or the BPM is smaller than the first count.

\* \* \* \* \*